(12) United States Patent
Lee et al.

(10) Patent No.: US 8,211,483 B2
(45) Date of Patent: Jul. 3, 2012

(54) COMPOSITION COMPRISING STARCH OR DIETARY FIBER FROM GRAMINEAE PLANT FOR PREVENTION AND TREATMENT OF ISCHEMIC DISEASES AND DEGENERATIVE BRAIN DISEASE

(75) Inventors: Jong Won Lee, Daegu (KR); Yae Sil Kim, Daegu (KR); Kyung Sik Song, Daegu (KR); Hyung Soo Han, Daegu (KR); Jung Hee Jang, Daegu (KR); Chae Ha Yang, Daegu (KR); Sun Ha Lim, Daegu (KR)

(73) Assignees: Hypoxi Co., Ltd., Daegu (KR); Sun Mok Institute Education Foundation, Daegu (KR)

( * ) Notice: Subject to any disclaimer, the term of this patent is extended or adjusted under 35 U.S.C. 154(b) by 0 days.

(21) Appl. No.: 12/666,969

(22) PCT Filed: Jul. 4, 2008

(86) PCT No.: PCT/KR2008/003975
§ 371 (c)(1),
(2), (4) Date: Dec. 28, 2009

(87) PCT Pub. No.: WO2009/005329
PCT Pub. Date: Jan. 8, 2009

(65) Prior Publication Data
US 2010/0143513 A1  Jun. 10, 2010

(30) Foreign Application Priority Data

Jul. 4, 2007 (KR) .................. 10-2007-0066887
Jul. 3, 2008 (KR) .................. 10-2008-0064291

(51) Int. Cl.
*A61K 36/00* (2006.01)
*A61K 36/899* (2006.01)
*A61K 31/715* (2006.01)

(52) U.S. Cl. ............ 424/750; 424/725; 514/54; 514/60

(58) Field of Classification Search .................. None
See application file for complete search history.

(56) References Cited

U.S. PATENT DOCUMENTS

| 5,444,042 A | * | 8/1995 | Bartus et al. | 514/2 |
| 6,294,520 B1 | * | 9/2001 | Naito | 514/23 |
| 2004/0224068 A1 | * | 11/2004 | Lee | 426/557 |

FOREIGN PATENT DOCUMENTS

| CN | 1836558 A | * | 9/2006 |
| JP | 2004065156 A | * | 3/2004 |
| KR | 2007045657 A | * | 5/2007 |
| WO | WO 9729764 A1 | * | 8/1997 |

OTHER PUBLICATIONS

Pengzhan et al, Polysaccharides from *Ulva pertusa* (Chlorophyta) and preliminary studies on their antihyperlipidemia activity, Journal of Applied Phycology (2003) vol. 15, No. 1, pp. 21-27.*

* cited by examiner

*Primary Examiner* — Qiuwen Mi
(74) *Attorney, Agent, or Firm* — Hogan Lovells US LLP

(57) ABSTRACT

The present invention relates to a composition comprising a starch or total dietary fiber which improves the cell viability, specifically, the inventive starch and total dietary fiber isolated from the extract of Gramineae plant and the components therefrom improved the cell viability when the cells were incubated under hypoxic condition, or in the presence of beta-amyloid and 6-hydroxydopamine treatment, as well as prevented and treated myocardiac infarction, cerebral infarction and vascular dementia, or alleviated memory loss, all of which were proven using rats as the respective animal models. Therefore, they can be used as therapeutics or health care food for preventing and treating ischemic diseases or degenerative brain diseases.

18 Claims, 6 Drawing Sheets

COMPOSITION COMPRISING STARCH OR DIETARY FIBER FROM GRAMINEAE PLANT FOR PREVENTION AND TREATMENT OF ISCHEMIC DISEASES AND DEGENERATIVE BRAIN DISEASE

This application is the U.S. National Phase under 35 U.S.C. §371 of International Application PCT/KR2008/003975, filed on Jul. 4, 2008, which claims priority to Korean Patent Application No. 10-2008-0064291, filed on Jul. 3, 2008 and Korean Patent Application No. 10-2007-0066887, filed on Jul. 4, 2007. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a composition comprising starch or total dietary fiber for preventing and treating ischemic diseases and degenerative brain diseases and the use thereof.

The present invention relates to a composition comprising at least one component selected from the group consisting of arabinoxylan, beta-glucan, arabinose and xylose for preventing and treating ischemic diseases and degenerative brain diseases.

BACKGROUND ART

Cerebral infarction and myocardial infarction, representative ischemic diseases, are caused by necrosis of the surrounding tissues that is also caused by clogging of cerebral or coronary arteries by thrombus, which was already narrowed by various factors such as hypertension, hyperlipidemia, diabetes, or smoking etc.

Cardiovascular disease, the leading cause of death worldwide each year, comprises approximately 30% of the total death, of which cerebral and myocardial infarction occupies 75%. Therefore, those two diseases and cancer are representative three diseases with the highest morbidity. The methods to decrease the morbidity caused by myocardial infarction and cerebral infarction are classified into two groups: one is to prevent vascular occlusion by treating hypertension and hyperlipidemia, and the other is to reduce necrosis of surrounding tissues when vascular occlusion occurs.

The best way to reduce necrotic region is to reperfuse the occluded arteries as soon as possible, for which thrombolytic agents have been used to dissolve thrombus or embolus, and subsequently, to reperfuse the occluded arteries. However, even reperfusion by the thrombolytic agents will not be effective in preventing infarction once tissues of heart and brain become necrotized after 3~6 hours of occlusion. In reality, the prompt reperfusion is difficult since patients can not reach the hospital within 3~6 hours after the occlusion. Furthermore, the already-damaged heart and brain do not regenerate well. Therefore, preventing the tissue damage until occluded arteries are reperfused at the hospital is another way to increase therapeutic efficacy, for which antiapoptotic agents can be an option because one cause of the cell death in cerebral and myocardial infarction is apoptosis (Crow M T et al., *Circ. Res.*, 95(10), pp 957-970, 2004; Friedlander R M, *N. Engl. J. Med.*, 348(14), pp 1365-1375, 2003).

Also, the damages of transplanted tissues resulting from kidney transplant (Daemen M A et al., *Transplantation*, 73(11), pp 1693-1700, 2002) and the plastic surgery (Gastman B R et al., P; *Ast. Reconstr. Surg.*, 111, pp 1481-1496, 2003) are induced by the apoptosis following an ischemia-reperfusion.

Additionally, the myocardiac injury can occur where the amount of oxygen required is more excessive than that of oxygen supplied by a pump-oxygenator, or subsequent cerebral injury can also occur by hypotension when a surgery is performed with cardiac arrest. For example, the heart failure caused by myocardial injury and the hemiplegia caused by brain damage may occur when the operations accompany with the occlusion of the part of blood vessels, for example, coronary artery bypass graft performed in case of the obstruction of coronary artery, and aneurysm surgery performed where the aneurysm occurs in cerebral arteries and aorta, etc. Actually, during the operative or interventional therapy for aortic aneurysm, side effects, such as ischemic heart disease, renal failure, paraplegia etc., occur in 3-16% of the patients. Accordingly, those side effects could be reduced if antiapoptotic agents are given before the operation.

The cause of apoptotic neuronal cell death has not been clarified well, however, there have been reported that apoptotic neuronal cell death is caused by decrease of ATP concentration and occurrence of edema, which occurs in case that transient ischemia following the blockage of oxygen and glucose supply to the brain is generated. It has been reported that apoptotic neuronal cell death in cerebral ischemia is induced by two mechanisms: one is excitatory neuronal cell death mechanism, whereby cerebral ischemia induces excessive accumulation of glutamate outside cells, influx of the glutamate into the cells, and excessive accumulation of calcium ion inside the cells (Kang T C et al., *J. Neurocytol.*, 30(12), pp 945-955, 2001), the other is oxidative neuronal cell death mechanism, whereby increase of free radicals, generated by sudden oxygen supply at ischemia-reperfusion induces damages to DNA and cytoplasm (Won M H et al., *Brain Res.*, 836(1-2), pp 70-78, 1999). Based on these kinds of mechanistic studies, there has been endeavor to screen inhibitors of apoptotic neuronal cell death or the mechanism thereof up to date. However, the effective inhibitors of apoptotic neuronal cell death has been not yet found.

It has been reported that minocycline, a tetracycline antibiotic which inhibits apoptosis under ischemic condition, has efficacy in treating ischemic diseases, such as cerebral infarction (Yrjanheikki J et al., *Proc. Natl. Acad. Sci. USA*, 96(23), pp 13496-13500, 1999), myocardial infarction (Scarabelli T M et al., *J. Am. Coll. Cardiol.*, 43(5), pp 865-874, 2004), ischemic acute renal failure (Wang J et al., *J. Biol. Chem.*, 279(19), pp 19948-19954, 2004), as well as degenerative brain diseases caused by neuronal cell apoptosis, such as Alzheimer's disease (Hunter C L, *Eur. J. Neurosci.*, 19(12), pp 3305-3316, 2004), Parkinson's disease (Wu D C et al., *J. Neurosci.*, 22(5), pp 1763-1771, 2002), amyotrophic lateral sclerosis (Zhu S et al., *Nature*, 417(6884), pp 74-78, 2002), Huntington's disease (Chen. M. et al., *Nat. Med.*, 6(7), pp 797-801, 2000) and spinal cord injury (Teng Y D et al., *Proc. Natl. Acad. Sci. USA*, 101(9), pp 3071-3076, 2004). The inventors of the present invention also confirmed that tetracyclines improved cell viability under similar ischemic conditions used in the present study (Korean Patent Registration No. 0404134; U.S. Pat. Nos. 6,716,822 & 6,818,625). In addition, other antibiotics such as aminoglycosides, quinolones also improved cell survival under ischemic condition, and G418 (geneticin), one of the aminoglycosides, in particular, showed efficacy in treating myocardial infarction (U.S. Pat.

No. 6,716,822). In the subsequent experiments, G418 inhibited apoptosis under ischemic conditions and showed efficacy in treating cerebral infarction as well. Based on these results, it has been expected that any samples showing the same cell survival effect under ischemic condition as that of G418 may have efficacy in treating ischemic diseases such as myocardial infarction, and also have efficacy in preventing and treating degenerative brain diseases that are caused by apoptosis. Through screening, the present inventors finally found that the crude extract of Gramineae plant, including *Triticum aestivum* L., improved cell viability under hypoxic conditions, and subsequently showed that the crude extract had efficacy in treating ischemic diseases such as cerebral and myocardial infarction, and degenerative brain diseases such as Alzheimer's disease, which was proven using ischemic and degenerative brain diseases animal models (Korea Patent Registration No. 10-0723950; and PCT/KR2006/000027).

The seeds of representative plants belonging to family Gramineae have been reported to contain about 10% moisture, carbohydrate component including 50-60% starch (25% in case of barley), 10-20% protein, 2-8% lipid, and 10-20% total dietary fiber (40% in case of barley) including 1-3% soluble dietary fiber (9% in case of barley) (Ranhotra G S et al., Cereal Chemistry 68(5), pp 556-558, 1991); or to contain 50-60% starch, 10-20% protein, 1-5% lipid, and 10-20% total dietary fiber (Grausgruber H et al., *In Genetic variation for plant breeding* (Vollmann J et al. (Eds.)), pp 23-26, Eucarpia & Boku, Vienna, 2004).

Arabinoxylan and beta-glucan are two major dietary fibers consisting of the cell wall of endosperm cell (Izydorczyk M S et al., *Carbohydrate Polymers*, 28, pp 33-48, 1995; Zekovic D B et al., *Crit. Rev. Biotech.*, 25, pp 205-230, 2005), whereby the cell wall of wheat (*Triticum aestivum* L.) (Philippe S et al., *Planta*, 224(2), pp 449-461, 2006) and rye (*Secale cereale* L.) (Vinkx C J A et al., *J. Cereal Sci.*, 24, pp 1-14, 1996) has been reported to contain more arabinoxylan than beta-glucan while that of oat (*Avena sativa* L.) (Miller S S et al., *Cereal Chem.*, 72(5), pp 421-427, 1995) and barley (*Hordeum vulgare* L.) (Kanauchi M and Bamforth C W, *Cereal Chem.*, 78(2), pp 121-124, 2001) has been reported to contain more beta-glucan than arabinoxylan. Generally, arabinoxylan is composed of arabinose and xylose; beta-glucan is composed of glucose (Izydorczyk M S et al., Carbohydr. Polym., 28, pp 33-48, 1995).

In addition to polymers, such as arabinoxylan and beta-glucan, the cell wall also comprises compounds showing high antioxidative effect, i.e., ferulic acid participating in crosslinking arabinoxylan molecules (Adams E L et al., *Carbohydr. Res.*, 340, pp 1841-1845, 2005), coumaric acid, vanillic acid, p-OH benzoic acid and syringic acid etc (Zhou K et al., *J. Agric. Food Chem.*, 52, pp 6108-6114, 2004; Clifford M N, *J. Sci. Food Agric.*, 79, pp 362-372, 1999).

Starch, a main reserve substance in the seed, root, stem, bulb, fruit etc of the green plants having abundant chlorophyll, is important as a carbohydrate source to higher animals. It is a colorless and odorless white powder having molecular weight ranging from 1,000,000 to 10,000,000, and having specific gravity of 1.65; exists as a granular form with different sizes and morphologies, depending on plants; and is a mixture of amylose and amylopectin with almost constant ratio in several kinds of starch, generally, 20-30% amylose and 70-80% amylopectin (Yoo et al., *Carbohydr. Polymers*, 49, pp 297-305, 2002). However, glutinous rice, waxy maize and etc., comprise little amylose and mainly amylopectin.

Although the inventors of the present inventions have reported that the crude extract of Gramineae plants, including wheat, improves cell viability under hypoxic conditions, and has an efficacy in improving and treating the ischemic diseases and degenerative brain diseases, using animal disease models (Korea Patent Registration No. 10-0723950; and PCT/KR2006/000027), there has been not disclosed that the purified starch, or total dietary fiber isolated from Gramineae plants and components of the dietary fiber, such as arabinoxylan, arabinose, xylose and beta-glucan, has an efficacy in improving and treating ischemic diseases and degenerative brain diseases in any of the above cited literatures, the disclosures of which are incorporated herein by reference.

Accordingly, the inventors of the present invention have completed the present inventions by investigating and confirming that starch or total dietary fiber isolated from Gramineae plants improved cell survival under hypoxic conditions, as well as in the presence of beta-amyloid or 6-hydroxydopamine, and that the starch or total dietary fiber also had an efficacy in improving and treating the ischemic diseases and degenerative brain diseases, using animal disease models.

DISCLOSURE

Technical Problem

The object of the present invention is to provide a pharmaceutical composition comprising a starch or total dietary fiber, and the use thereof to prevent and treat ischemic diseases and degenerative brain diseases induced by apoptosis under ischemic condition.

Technical Solution

Accordingly, it is an object of the present invention to provide a pharmaceutical composition comprising a starch or total dietary fiber as an active ingredient for the prevention and treatment of ischemic diseases and degenerative brain diseases.

Also, it is an object of the present invention to provide a health care food comprising a starch or total dietary fiber as an active ingredient for the prevention and improvement of ischemic diseases and degenerative brain diseases.

The present invention also provides a use of starch or total dietary fiber for the manufacture of pharmaceutical composition to prevent and treat ischemic diseases and degenerative brain diseases caused by apoptosis in mammal or human in need thereof.

The present invention provides a method of preventing and treating ischemic diseases and degenerative brain diseases in a human or mammal suffering from ischemic diseases and degenerative brain diseases by administering an effective amount of starch or total dietary fiber, together with a pharmaceutically acceptable carriers or adjuvants thereof.

Also, the present invention provides a pharmaceutical composition comprising at least one component selected from the group consisting of arabinoxylan, beta-glucan, arabinose and xylose as active ingredients for the prevention and treatment of ischemic diseases and degenerative brain diseases.

Also, the present invention provides a health care food comprising at least one component selected from the group consisting of arabinoxylan, beta-glucan, arabinose and xylose as active ingredients for the prevention and treatment of ischemic diseases and degenerative brain diseases.

The present invention also provides a use of at least one component selected from the group consisting of arabinoxylan, beta-glucan, arabinose and xylose for the manufacture of pharmaceutical composition to prevent and treat ischemic diseases and degenerative brain diseases caused by apoptosis in a mammal or human in need thereof.

The present invention provides a method of preventing and treating ischemic diseases and degenerative brain diseases in a human or mammal suffering from ischemic diseases and degenerative brain diseases by administering an effective amount of at least one component selected from the group consisting of arabinoxylan, beta-glucan, arabinose and xylose, together with a pharmaceutically acceptable carriers or adjuvants thereof.

The term "ischemic diseases" disclosed herein comprises various ischemic diseases such as myocardial infarction, cerebral infarction, ischemic acute renal failure, ischemic acute hepatic failure, diabetic foot ulcer, diabetic nephropathy, and ischemic diseases resulting from the side effect of surgical operation or organ-tissue injury, preferably, myocardial infarction, cerebral infarction etc.

The term "the ischemic disease resulting from the side effect of surgical operation" disclosed herein comprises an ischemic heart failure, ischemic renal failure, ischemic hepatic failure or ischemic stroke, preferably, ischemic heart failure, ischemic stroke etc.

The term "organ-tissue injury" disclosed herein is the ischemia-reperfusion injury occurring when organ surgery or transplantation, or reconnection of parts of body severed by an accident is performed.

Above described "organ" comprises internal organs, for example, kidney, liver, pancreas, lung, heart etc.

The term "degenerative brain diseases" disclosed herein comprises various degenerative brain diseases such as Alzheimer's disease, vascular dementia, Parkinson's disease, amyotrophic lateral sclerosis, Huntington's disease, Pick's disease, Creutzfeldt-Jakob disease or spinal cord injury, preferably, Alzheimer's disease, vascular dementia, Parkinson's disease etc.

The term "starch" disclosed herein include various starch purified from Gramineae plants such as *Triticum aestivum* L., *Tritici levis* semen, *Secale cereale* L., *Oryza sativa* L. (rice), *Hordeum vulgare* var. *hexastichon* ASCH., malt, *Avena sativa*, *Zea mays* L., *Sorghum bicolor* MOENCH, *Coix lacryma-jobi* var. *mayuen* STAPF, *Panicum miliaceum* L. or *Setaria italica* Beauv. or potato, preferably, starch purified from *Triticum aestivum* L., *Zea mays* L., *Hordeum vulgare* var. *hexastichon* ASCH., rice or potato, more preferably, starch purified from *Triticum aestivum* L., starch purified from *Zea mays* L., starch purified from rice or soluble starch purified from potato, furthermore preferably, starch purified from *Triticum aestivum* L., starch purified from *Zea mays* L., starch purified from rice or soluble starch purified from potato, all with the molecular weight ranging from 1,000,000 to 10,000,000.

The term "total dietary fiber" disclosed herein include total dietary fiber purified from Gramineae plants such as *Triticum aestivum* L., *Tritici levis* semen, *Secale cereale* L., *Oryza sativa* L., *Hordeum vulgare* var. *hexastichon* ASCH., malt, *Avena sativa*, *Zea mays* L., *Sorghum bicolor* MOENCH, *Coix lacryma-jobi* var. *mayuen* STAPF, *Panicum miliaceum* L., *Setaria italica* Beauv. or potato, preferably, total dietary fiber purified from *Triticum aestivum* L., *Secale cereale* L., *Hordeum vulgare* var. *hexastichon* ASCH., *Zea mays* L. or *Oryza sativa* L., more preferably, total dietary fiber purified from *Triticum aestivum* L. consisting of arabinoxylan, beta-glucan and arabinogalactan with the ratio of 5-20:1:1-10 by relative weight %, furthermore preferably, total dietary fiber purified from *Triticum aestivum* L. consisting of arabinoxylan and beta-glucan with the molecular weight ranging from 50,000 to 400,000 Dalton.

The term "arabinose" and "xylose" disclosed herein comprise both L- and D-form, preferably, the forms produced in nature, namely arabinose comprises L-form, and xylose comprises D-form.

Hereinafter, the present invention is described in more detail.

The inventive starch can be prepared in detail by the following procedures;

Drying and crushing the seeds of Gramineae plants, preferably *Triticum aestivum* L., *Tritici levis* semen, *Secale cereale* L., brown rice, *Hordeum vulgare* var. *hexastichon* ASCH., malt, *Avena sativa*, *Zea mays* L., *Sorghum bicolor* MOENCH, *Coix lacryma-jobi* var. *mayuen* STAPF, *Panicum miliaceum* L. or *Setaria italica* Beauv, more preferably *Triticum aestivum* L., to powder; mixing the powder with 10 to 100%, preferably, approximately 50 to 70% volume of distilled water to make dough; wrapping the dough with nylon bolting cloth, pressing the dough under running water for the starch to be eluted, and centrifuging the elutant to collect the precipitates; finally, purifying the inventive starch by suspending the precipitates in distilled water, and centrifuging altogether to collect the inventive starch of the present invention.

Also, the inventive total dietary fiber can be prepared in detail by the following procedures;

Drying and crushing the seeds of Gramineae plants, preferably *Triticum aestivum* L., *Tritici levis* semen, *Secale cereale* L., brown rice, *Hordeum vulgare* var. *hexastichon* ASCH., malt, *Avena sativa*, *Zea mays* L., *Sorghum bicolor* MOENCH, *Coix lacryma-jobi* var. *mayuen* STAPF, *Panicum miliaceum* L. or *Setaria italica* Beauv, more preferably, *Triticum aestivum* L., brown rice or *Zea mays* L. to powder; mixing the powder with approximately 1 to 15-fold, preferably, approximately 5 to 10-fold volume of distilled water, lower alcohol with $C_1$-$C_4$, such as methanol, ethanol, butanol etc, or the mixture thereof, preferably, distilled water or the mixture of water and $C_1$-$C_4$ lower alcohol with the ratio ranging from about 1:0.1 to 1:10, more preferably, distilled water or the mixture of water and ethanol with the ratio ranging from about 1:0.1 to 1:10 to subject the extraction using extraction methods, such as the cold water, hot water, ultra-sonication, reflux-refrigerated, electric brewing pot extraction at the temperature ranging from 20° C. to 100° C., preferably, 25° C. to 100° C., for the period ranging from 0.5 to 48 hours, preferably 1 to 24 hours with 1 to 12 times, preferably, 3 to 4 times; filtering and concentrating the filtrate with rotary evaporator, at the temperature ranging from 20° C. to 100° C., preferably 40° C. to 70° C., and then drying the concentrate by vacuum freeze-drying to obtain dried crude extract powder; and removing saccharide with ethanol, preferably, 85% ethanol if sugar content is over 50% of total dried weight of crude extract; dissolving the ethanol-washed and dried residue in 10 to 70-fold, preferably, 30 to 50-fold buffer solution, and treating with alpha-amylase for 10 to 60 mins, preferably, 25 to 45 mins at the temperature ranging from 50° C. to 120° C., preferably 70° C. to 90° C., treating with protease to remove proteins at the temperature ranging from 30° C. to 90° C., preferably 50° C. to 70° C., and after adjusting the solution to pH 4.1~4.5, preferably, pH 4.2-4.4 by using acetic acid, treating with amyloglucosidase at the temperature ranging from 20° C. to 100° C., preferably 50° C. to 70° C.; finally, precipitating the solution by adding 1-7 fold, preferably, 3-5 fold volume of ethanol, to obtain the precipitated total dietary fiber of the present invention.

The present invention provides a pharmaceutical composition comprising the starch or total dietary fiber as an active ingredient prepared by the above-described preparation method for the prevention and treatment of ischemic and degenerative brain diseases.

The starch, total dietary fiber, arabinoxylan, beta-glucan, arabinose and xylose of the present invention can be obtained by the well-known isolation or purification method in the art or from commercial market or companies.

The inventive starch or total dietary fiber can be used safely for a long term because of almost no side effects and no toxicity.

The pharmaceutical composition comprising inventive starch or total dietary fiber can also comprise proper carriers, adjuvants and diluents, which are conventionally used in manufacturing the pharmaceutical composition.

The pharmaceutically acceptable carriers, adjuvants or diluents that can be included in the pharmaceutical composition containing the inventive starch or total dietary fiber are lactose, dextrose, sucrose, sorbitol, mannitol, xylitol, erythritol, maltitol, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil.

The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixir, pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging 10 mg/kg, preferably, 0.1 to 1000 mg/kg by weight/day of the inventive extract or composition of the present invention. The dose may be administered in single or divided into several times per day.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

The present invention provides a health care food comprising the starch or total dietary fiber as an active ingredient for the prevention and improvement of ischemic diseases and degenerative brain diseases.

The term "health care food" disclosed herein means the manufactured and processed food containing the active ingredients or components showing useful functions to human health, whereby "functions to human health" means the beneficial effect or advantageous effect on human health through its physiological action or regulation on human according to the structure and function of human body.

The health care food of the present invention for the prevention and improvement of ischemic diseases and degenerative brain diseases comprises the above starch or total dietary fiber as 0.01 to 95% by weight, preferably 1 to 80% by weight based on the total weight of the composition.

Also, pharmaceutically administrative form such as powder, granule, capsule, tablet, suspension, emulsion, syrup etc, or health care food such as health beverage etc for the prevention and improvement of ischemic diseases and degenerative brain diseases may be manufactured and processed.

Providing that the health beverage composition of the present invention contains the above-described ingredient as an essential component in the indicated ratio, there is no particular limitation on the other liquid components in the conventional beverage, wherein the other component can be various deodorant or natural carbohydrate etc. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As other deodorants than aforementioned ones, natural deodorant such as taumatin, stevia extract such as levaudioside A, glycyrrhizin et al., and synthetic deodorant such as saccharin, aspartam et al., may be used favorably. The amount of the above-described natural carbohydrate generally ranges from about 1 to 20 g, preferably 5 to 12 g in 100 ml of the present beverage composition.

Other components than aforementioned components are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. Other components beside the aforementioned ones may be fruit for preparing natural fruit juice, fruit juice beverage and vegetable beverage, wherein the components can be used independently or in combination. The ratio of the components is not so important but has ranges generally from about 0 to 20 w/w % per 100 w/w % present composition.

Also, the inventive starch and total dietary fiber can be added to food, additive or beverage for the prevention of ischemic diseases and degenerative brain diseases, wherein the amount of the above-described extract in food or beverage may generally range from about 0.01 to 15 w/w % of total weight of health care food, and from 0.02 to 5 g, preferably 0.3 to 1 g in 100 ml of the health beverage.

Advantageous Effects

The starch or total dietary fiber of the present invention improved the cell viability when respective cells were cultured under hypoxic condition, or in the presence of beta-amyloid and 6-hydroxydopamine, as well as prevented and treated myocardiac infarction, cerebral infarction and vascular dementia, or alleviated memory loss, all of which were proven using rats as the respective animal models. Therefore, the starch or total dietary fiber of the present invention can be used as therapeutics or health care food for preventing and treating ischemic diseases or degenerative brain diseases.

BEST MODE

The present invention is more specifically explained by the following examples. However, it should be understood that the present invention is not limited to these examples in any manner.

The following Reference Examples, Examples and Experimental Examples are intended to further illustrate the present invention without limiting its scope.

MODE FOR INVENTION

Reference Example 1

Materials

The starch purified from corn (*Zea mays* L.) (Catalog No. 54180; designated as "SC" hereinafter), rice (*Oryza sativa* L.), (Catalog No. 57260; designated as "SR" hereinafter), purified soluble starch (Catalog No. 59765; designated as "SS" hereinafter) and arabinose (Catalog No. A3256: L(+) form, MW 150.13) were purchased from Sigma (USA). Medium viscosity arabinoxylan (Catalog No. P-WAXYM; from wheat, viscosity:25 cSt, MW: 270,000 Dalton), medium viscosity beta-glucan (Catalog No. P-BGBM: from barley, viscosity: 28 cSt, MW: 260,000 Daltons) were purchased from Megazyme (Ireland). Xylose (Catalog No. 95729: D(+) form, MW 150.13) was purchased from Fluka (Germany).

Reference Example 2

Preparation of Experimental Animal

Male Sprague-Dawley (SD) rats weighing from 250-300 g were purchased from Hyochang Science Co. (Korea) and bred in animal breeding room under 12 hours cycle of day/night at 21±2° C. ad libitum with free access to water and animal feed. The animals were handled for 10 mins prior to experiment.

Example 1

The Preparation of Crude Extracts of the Gramineae Plants 100 g of *Triticum aestivum* L. purchased from the market was washed, mixed with 2 l of water and extracted two times using oriental herb medicine electric brewing pot (Daewoong oriental herb medicine electric brewing pot DWP-2000, Daewoong). The solution was filtered and 2 l of the filtered extract obtained was lyophilized to get 22 g of dried crude extract of *Triticum aestivum* L. (designated as "HY6228" hereinafter). And the same procedure described above was applied to dried brown rice, and *Zea mays* L., 100 g of each, to obtain 20 g and 9 g of crude extract of brown rice, and *Zea mays* L., respectively (designated as "HY6228A" and "HY6228F" hereinafter).

To remove low molecular weight substances, with molecular weight smaller than 6,000 to 8,000 Dalton, from the crude extract of *Triticum aestivum* L., 10 g of HY6228 was suspended in 100 ml of distilled water, poured into dialysis membrane (Spectra/Por 1-132675, Spectrumlabs), and dialyzed with stirring at 4° C. in 500 ml of distilled water for 24 hours, with replacement of 500 ml of fresh distilled water three times for 3 days. The solution in the membrane was lyophilized to obtain 6.66 g of purified water extract of *Triticum aestivum* L. containing high molecular weight substances (designated as "HY6228d" hereinafter).

Example 2

The Preparation of Inventive Total Dietary Fiber of the Gramineae Plants

The total dietary fiber containing ash component has been isolated from the crude extract of *Triticum aestivum* L. prepared in Example 1 (HY6228) according to procedure disclosed in the literature (Lee S. C. et al., *J. Assoc. off. Anal. Chem.*, 75, pp 395-416, 1992; Prosky L et al., *J. Assoc. Off. Anal. Chem.*, 71, pp 1017-1023) and the manual of Megazyme Co. Ltd (TDFR 06/10).

10 g of HY6228 prepared in Example 1 was poured in 500 ml bottle, and 400 ml of MES/TRIS buffer solution (each of 0.05 M, pH 8.0, 24° C.) was added thereto. The solution was mixed thoroughly, and then 70 microliter of alpha-amylase (23 mg/ml Termamyl, 930 U/mg, 24° C.) was added thereto to react at 80° C. for 35 mins in water bath. After the reaction, the solution was cooled to 60° C. and 1000 microliter of protease (~350 U/ml Megazyme Cat. No. E-BSPRT) was added thereto to react at 60° C. for 30 mins in water bath. The solution was adjusted to pH 4.3 with 3 M acetic acid and 2000 microliter of amyloglucosidase (3300 U/ml, Megazyme Cat. No. E-AMGDF) was added thereto to react at 60° C. for 30 mins in water bath. The solution was mixed with 1600 ml of 95% EtOH preheated to 60° C., and left at room temperature for 60 mins, without stifling. The solution was centrifuged to collect the precipitate, and the precipitates were dried to obtain 2.3 g of total dietary fiber (TDF).

Example 3

The Analysis of Sugar Components of TDF Comprising Arabinoxylan and Beta-Glucan etc To determine the composition of TDF comprising arabinoxylan (arabinose and xylose) and beta-glucan, the amount of arabinose, xylose, glucose and galactose in the TDF was analyzed at Carbohydrate Material Laboratory in Seojeng University (http://www.carbo.or.kr).

2 mg/ml of TDF was subjected to acid hydrolysis for 4 hours at 100° C. with trifluoroacetic acid. 10 microliter (total 0.2 microgram) of hydrolyzed solution was injected into CarboPac™PA1 column (HPAEC-PAD system, Dionex, USA), and eluted with 18 mM NaOH at the flow rate of 1.0 ml/min (Houben R et al., *J. Cereal Sci.*, 26, pp 37-46, 1997).

Figure 1:
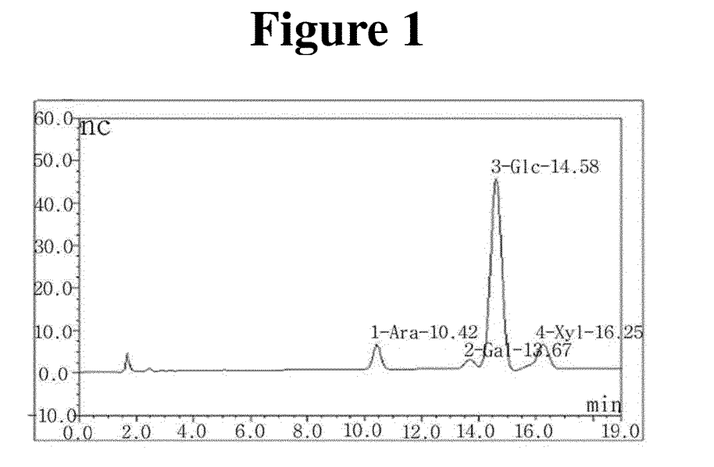
FIG. 1 shows the analysis data of the sugar composition of the arabinoxylan and beta-glucan etc comprising inventive TDF.

As shown in FIG. 1, arabinoxylan (Ara), galactose (Gal), glucose (Glc) and xylose (Xyl) were detected in eluting order, which was confirmed by comparing elution time of sugar standard. The amount of each component calculated from the peak area corresponded to 69.5 μmol (10.4 ng), 27.0 μmol (4.9 ng), 652.7 μmol (117.5 ng) and 81.6 μmol (12.2 ng), respectively. Because galactose is derived from arabinogalactan, and the amount of arabinose in arabinogalacton corresponds to 0.7-fold of that of galactose (Virkki L et al., *Carbohydr. Res.*, 343, pp 521-529, 2008), the amount of arabinose became 7 ng after we subtracted the amount of arabinose in arabinogalactan (3.4 ng) from that of the measured arabinose (10.4 ng). Therefore, the weight ratio of ara/xyl was 0.58, which is identical to the data disclosed in reference (Ordax-Ortiz J J et al., *J. Ceral Sci.*, 42, pp 119-125, 2005). Finally, the amount of arabinoxylan in 0.2 microgram (200 ng) of TDF was 19.2 ng (9.6%, weight ratio), and the amount of arabinogalactan was 8.3 ng (4.1%, weight ratio).

In the meanwhile, since the glucose in TDF is derived not only from beta-glucan, but also from cellulose and resistant starch, the amount of beta-glucan in TDF was determined using mixed-linkage beta-glucan assay procedure (McCleary method), for which mixed-linkage beta-glucan assay kit (Megazyme K-BGLU 04/06) was used. In this method, lichenase hydrolyzes beta-glucan partially, and then beta-glucosidase hydrolyzes the partially hydrolyzed beta-glucan completely to glucose. The amount of glucose produced was determined by measuring absorbance at 510 nm after the glucose was reacted with glucose oxidase and peroxidase. From the experiment, the beta-glucan within the TDF was measured to be approximately 1.1% (w/w %).

In summary of the above results, arabinoxylan (ara/xyl=0.58), beta-glucan and arabinogalactan was 9.6, 1.1, and 4.1% (w/w %), respectively, and glucose beside beta-glucan was 115.3 ng (57.7%, w/w %).

Example 4

The Preparation of Inventive Starch from the Gramineae Plants

The inventive starch (SW) has been isolated from wheat flour according to the procedure disclosed in the literature (Van Der Borght et al., *J. Cereal Sci.* 41, pp 221-237, 2005).

Water was added to 50 g of wheat flour to make dough having 50% water content, and the dough was wrapped with 50 micrometer Nylon bolting cloth. The dough in the cloth was pressed under running water until no more turbid water appeared. The elutant was centrifuged to collect the precipitates to obtain inventive starch of the present invention (designated as "SW" hereinafter).

Experimental Example 1

Measurement of Improving Effect of Starch on Cell Viability (in Vitro) Under Hypoxic Condition To investigate effect of inventive crude extract, starch and total dietary fiber purified therefrom on HepG2 cell viability under hypoxic condition, the following MTT assay was performed by the procedure disclosed in literature (Hoffman R. M., *Cell Biology* (Celis J E (Ed.), Vol. 1, pp 369-370, Academic Press, New York, 1994) with minor modification.

HepG2 cells (human hepatoma cell line, ATCC HB 8065, $2 \times 10^5$ cells/800 μl) were seeded onto each well of 12-well plate and incubated in EMEM (Eagle's minimum essential medium; Invitrogen, USA) supplemented with penicillin G sodium (100 Units/L, Invitrogen, USA), streptomycin sulfate (100 mg/L, Invitrogen, USA) and 10% (w/v) fetal bovine serum (Invitrogen, USA); and incubated at 37° C. for 48 hours in 5% $CO_2$ incubator. After the media were changed with fresh medium, the media were added with various concentrations of inventive crude extract, starch and total dietary fiber dissolved in 100% DMSO to the final concentrations of crude extract, and starch: 100, 200, 400 and 800 microgram/ml; TDF: 100 and 1000 microgram/ml as a test group, or with none as a negative control group. The cells were further incubated under hypoxic condition (oxygen conc.: 1%) for another 2 days. Finally, the result of the MTT assay was obtained as shown in FIGS. 2a and 2b.

Figure 2:
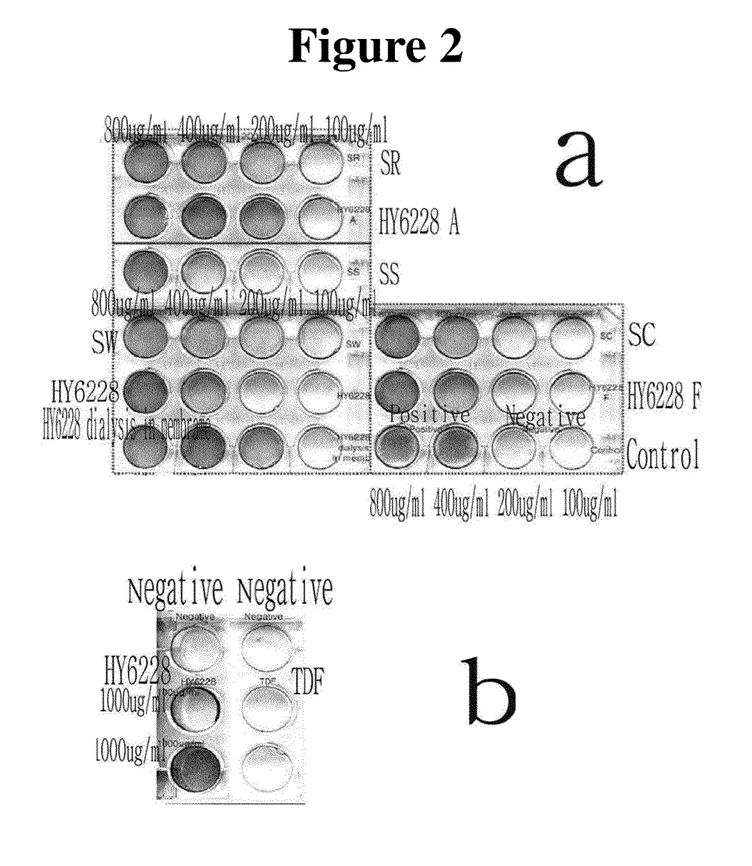
FIG. 2a shows the improving effect of addition of various concentrations of the crude extract and inventive starch isolated from Gramineae plants (*Triticum aestivum* L., brown rice and *Zea mays* L.) on HepG2 cell viability cultured under hypoxic condition.
FIG. 2b shows the effect of addition of various concentrations of inventive TDF purified from the crude extract of *Triticum aestivum* L. on HepG2 cell viability cultured under hypoxic condition.

As shown in FIG. 2a, SR, HY6228A, SW and HY6228d over 200 microgram/ml, HY6228, SC and HY6228F over 400 microgram/ml, and SS over 800 microgram/ml, respectively, improved cell viability.

In addition, as shown in FIG. 2b, HY6228 at the concentration of 1000 microgram/ml showed strong improving effect of cell viability.

As mentioned above, not only the inventive crude extract of *Triticum aestivum* L., brown rice, and *Zea mays* L. but also the starch purified therefrom showed potent improving effect on the cell viability under hypoxic condition. However, TDF did not improve the cell viability under hypoxic condition. According to prior art (Korea Patent Registration No. 10-0723950 and PCT/KR2006/000027), the crude extract of *Triticum aestivum* L., which improves the cell viability under hypoxic condition, showed therapeutic efficacy not only against ischemic diseases such as cerebral infarction etc, but also against degenerative brain diseases such as Alzheimer's disease. Based on these results, the inventive starch from Gramineae plants, which also improves the cell viability under hypoxic condition, can be predicted to be effective to treat the diseases.

Experimental Example 2

Effect of Starch and Total Dietary Fiber on the Beta-Amyloid-Induced Cytotoxicity (In Vitro)

To identify the neuroprotective effect of inventive crude extract, starch and total dietary fiber on the cytotoxicity induced by beta-amyloid, which is regarded as one of the main causes of Alzheimer's disease, the following MTT assay was performed by the procedure disclosed in the literature (Hoffman R. M., *Cell Biology* (Celis J E (Ed.), Vol. 1, pp 369-370, Academic Press, New York, 1994) with minor modification.

SH-SY5Y cells (human neuroblastoma cell line, ATCC CRL-2266, $4 \times 10^4$ cells/300 microliter/well) were seeded onto 48 well plates and incubated in Dulbecco's modified Eagle Medium/F12 90% medium (Invitrogen, USA) supplemented with penicillin G sodium (100 Units/L, Invitrogen, USA), streptomycin sulfate (100 mg/L, Invitrogen, USA) and 10% (w/v) fetal bovine serum (Invitrogen, USA); incubated at 37° C. in 5% $CO_2$-95% air incubator for 48 hours. After changing the media, the cells were treated with beta-amyloid to the final concentrations of 0, 2.5, 7.5 and 25 microM for 24 hours in the absence (designated as $A\beta_{25-35}$ alone group hereinafter) or presence with inventive starch isolated from *Triticum aestivum* L. (final concentration: 125 microgram/ml; designated as $A_{25-35}$+SW group hereinafter) or soluble starch (final concentration: 125 microgram/ml; designated as $A_{25-35}$+SS group hereinafter) which were made from 50 microgram/ml stock solutions in DMSO (See FIGS. 3a & 3b). After incubation, cells were treated with MTT solution (final concentration of 1 mg/ml) for 2 hours. The dark blue formazan in viable cells was dissolved in DMSO and absorbance at 540 nm was measured by a microplate reader (FLUOstar OPTIMA, BMG LABTECH, GERMANY).

Based on the above-mentioned result, to further examine the protective effects of the crude extract of *Triticum aestivum* L. or starches isolated from Gramnieae plants against the beta-amyloid-induced cytotoxicity, the concentration of beta-amyloid was fixed to 25 microM. The crude extract of *Triticum aestivum* L. (HY6228, shown as HY in FIG. 3c; 250 microgram/ml) and starches isolated from Gramnieae plants (SS, SC, SR and SW; 125 microgram/ml) were added thereto to incubation (See FIG. 3c). We also have examined the cell viability improving effect of total dietary fiber (TDF; 500, 1000 microgram/ml) in the presence of 10 microM of beta-amyloid (See FIG. 3d).

Figure 3:
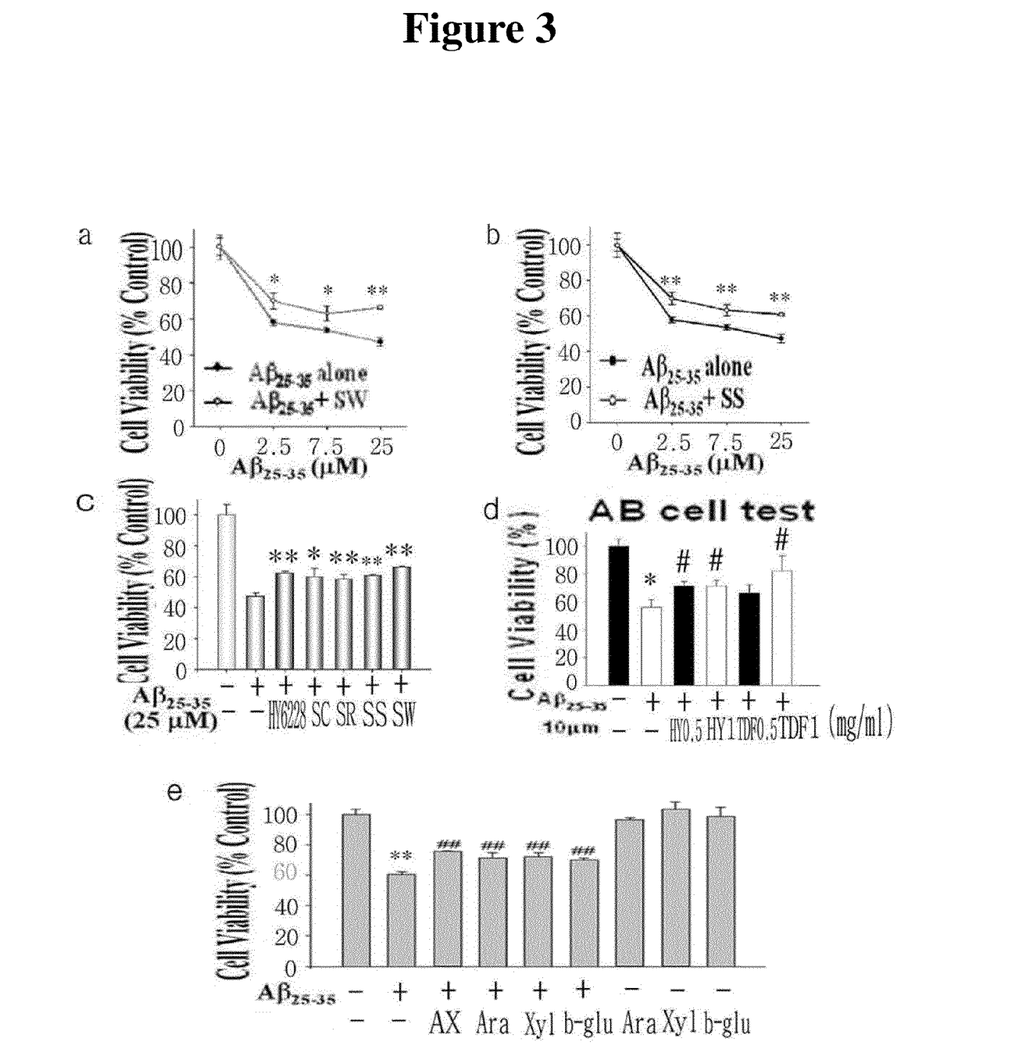
FIG. 3a shows the improving effect of addition of various concentrations of the inventive starch purified from *Triticum aestivum* L. on SH-SY5Y cell viability cultured with various concentrations of beta-amyloid.
FIG. 3b shows the improving effect of addition of various concentrations of the soluble starch on SH-SY5Y cell viability cultured with various concentrations of beta-amyloid.
FIG. 3c shows the improving effect of addition of various concentrations of the crude extract of *Triticum aestivum* L. (HY6228) and inventive starches purified from Gramineae plants (SC: corn; SR: rice; SS: soluble starch; SW: *Triticum aestivum* L.) on SH-SY5Y cell viability cultured with 25 microM of beta-amyloid.
FIG. 3d shows the improving effect of addition of various concentrations of the inventive total dietary fiber including ash component on SH-SY5Y cell viability cultured with 10 microM of beta-amyloid.
FIG. 3e shows the improving effect of addition of arabinoxylan and beta-glucan comprising total dietary fiber, and arabinose and xylose comprising arabinoxylan on SH-SY5Y cell viability cultured with 15 microM of beta-amyloid.

In addition, arabinoxylan (AX; 500 microgram/ml), arabinose (Ara; 250 microgram/ml), xylose (Xyl; 250 microgram/ml) and beta-glucan (b-glu; 20 microgram/ml) were added to the media in the presence of 15 microM beta-amyloid (See FIG. 3e).

As the results, as shown in FIG. 3a and FIG. 3b, the group treated with 0-25 microM beta-amyloid in combination with 125 microgram/ml of SW (See FIG. 3a) or SS (See FIG. 3b) significantly reduced the beta-amyloid-induced cytotoxicity at the concentrations of more than 2.5 microM [$p<0.05$ (*) or $0.01$ (**)]. Furthermore, the test groups treated with inventive starch and TDF together with beta-amyloid effectively improved the cell viability (See FIGS. 3c & 3d). Also as shown in FIG. 3e, cell viability was 60.4% when cells were treated with 15 microM beta-amyloid alone, however the cell viability was improved to 75.5, 71.1, 72.1 and 70% when arabionxylan, arabinose, xylose and beta-glucan were present in the media, respectively [$p<0.05$].

From the above results, it has been confirmed that the inventive starch and total dietary fiber of the present invention showed improving effect on cell viability by decreasing cytotoxicity caused by beta-amyloid, similarly to the crude extract of *Triticum aestivum* L. (HY6228). Accordingly, the inventive starch and total dietary fiber of the present invention can be useful in treating Alzheimer's disease occurring by the accumulation of beta-amyloid.

Experimental Example 3

Effect of Crude Extract on the 6-Hydroxydopamine-Induced Cytotoxicity (In Vitro)

To identify the neuroprotective effect of inventive crude extract of *Triticum aestivum* L. (HY6228) on the cytotoxicity induced by 6-hydroxydopamine well-known as an experimental inducing factor of Parkinson's disease (Guo S et al., Free Radic. Biol. Med., 39(5), pp 682-695, 2005), the following MTT assay was performed with a similar method disclosed in Experimental Example 2.

SH-SY5Y cells (human neuroblastoma cell line, ATCC CRL-2266, $6 \times 10^4$ cells/300 microliter/well) were seeded onto 48 well plates and incubated in Dulbecco's modified Eagle Medium/F12 90% medium (Invitrogen, USA) supplemented with penicillin G sodium (100 Units/L, Invitrogen, USA), streptomycin sulfate (100 mg/L, Invitrogen, USA) and 10% (w/v) fetal bovine serum (Invitrogen, USA); incubated at 37° C. in 5% $CO_2$-95% air incubator for 48 hours. After changing the media, the cells were treated with 6-hydroxydopamine (6-OHDA; Sigma-Aldrich Co., USA) to the final concentration of 250 microM and incubated for 24 hours. Inventive crude extract of *Triticum aestivum* L. (HY6228) was treated to the final concentration of 0.25, 0.5, 1 mg/ml, 30 minutes prior to 6-OHDA treatment. After incubation, cells were treated with MTT solution (final concentration of 1 mg/ml) for 2 hours. The dark blue formazan in viable cells was dissolved in DMSO and absorbance at 540 nm was measured by a microplate reader (FLUOstar OPTIMA, BMG LABTECH, GERMANY).

Figure 4:
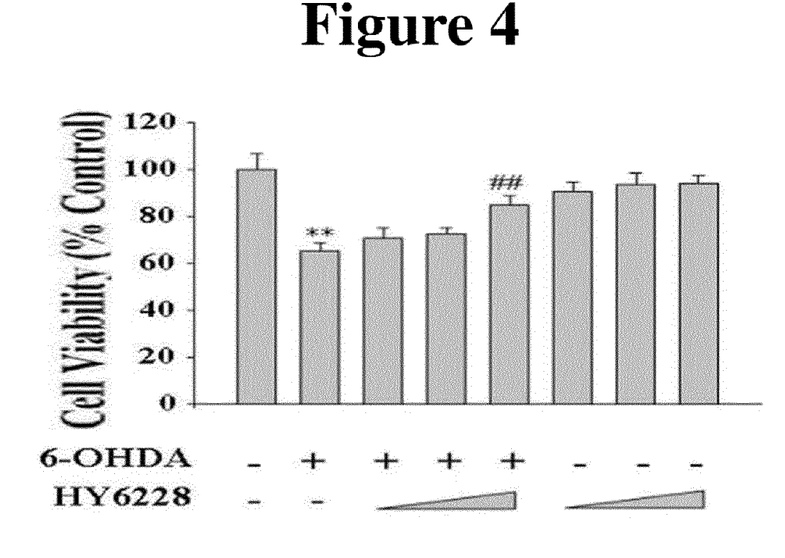
FIG. 4 shows the improving effect of addition of various concentrations of the crude extract of *Triticum aestivum* L. (HY6228) on SH-SY5Y cell viability cultured with 250 microM 6-hydroxydopamine.

At the results, as shown in FIG. 4, the group treated with 1 mg/ml HY6228 in combination with 6-OHDA exhibited significantly increased cell viability compared with 6-OHDA alone group [p<0.01].

In summary, it has been confirmed that the inventive crude extract isolated from *Triticum aestivum* L. showed improving effect on cell viability by decreasing cell cytotoxicity caused by 6-hydroxydopamine, and therefore it can be effective in treating Parkinson's disease.

Experimental Example 4

Effect of Starch and Total Dietary Fiber Administered Orally on Myocardial Infarction (In Vivo)

The therapeutic efficacy of inventive starch and total dietary fiber on myocardial infarction was measured in myocardial infarction-induced rat model, using experiment rats prepared in Reference Example 1, in accordance with the procedure disclosed in the literature (Haisong J et al., *Circulation*, 97, pp 892-899, 1998), with minor modification.

SD rats prepared in Reference Example 1 were anesthetized with 10 mg/kg ketamine (Yuhan Corp., KOREA) and 5 mg/kg xylazine (Sigma, USA) and intubated endotracheally. The rats were connected to a respirator through a tracheotomy, and the heart was rapidly exteriorized through a left thoracotomy and pericardial incision. The upper region of left coronary artery (LAD) was ligated by passing a 5-0 prolene thread under LAD and tightening polyethylene tubing 50 (PE 50), resulting in ischemia. After 30 min of ischemia, 3 hours of reperfusion followed, after the tightened PE 50 was loosened. After the ischemia-reperfusion, the PE 50 was tightened again to induce ischemia, and then 2 ml of 1% Evans blue dye solution was infused intravenously to circulate whole body. Then the heart was isolated, cut into the width of 2-3 mm after the right atrium and right ventricle of the heart were removed. Then the stained (LV-AAR) and unstained area (AAR) of cross sectioned tissue was measured by using image analysis system (Quantity One 4.2, Bio-Rad, USA) to calculate the area at risk (AAR/LV, %). Then, the tissue was stained with 1% TTC (2,3,5-triphenyltetrazolium chloride, Sigma, USA) at 37° C. for 15 mins, fixed with 10% formalin solution. The infarcted area (IA/LV, %) was determined by measuring necrotic white area (IA) and total left ventricle area (LV). The ratio of IA to AAR of test samples and control group was compared to test efficacy.

The inventive starch, total dietary fiber, and representative components of the fiber mixed with food were administered orally, and the size of infarcted area was measured. To determine the proper dose with safety and maximum efficacy at the same time, the minimum dose calculated from the result obtained in Experimental Example 1 was set as a starting point, and the dose was increased according to two-fold increasing method, i.e., 100, 200 and 400 mg/kg.

Three days before the induction of ischemia, 400 mg/kg/day of HY6228 or inventive starch, or 10 mg/kg/day of inventive total dietary fiber, or 10 mg/kg/day of its components, such as arabinoxylan, beta-glucan, arabinose and xylose, was fed with 20 g of food with free access. After induction of myocardial infarction with 3 hours of reperfusion, the infarcted area was measured, the value of IA (% AAR) was calculated, and then efficacy of the inventive starch and total dietary fiber was compared with each other.

Figure 5:
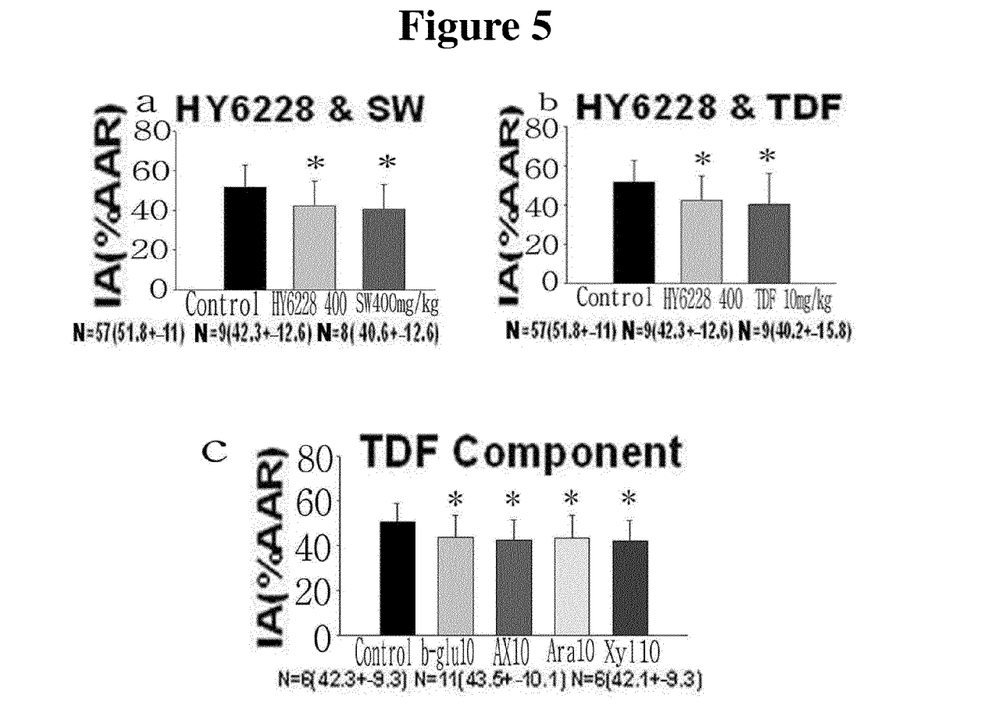
FIG. 5a represents the inhibitory effect of the orally administered inventive starch purified from *Triticum aestivum* L. on the myocardial infarction in myocardial-infraction animal model.
FIG. 5b represents the inhibitory effect of the orally administered inventive TDF purified from *Triticum aestivum* L. on the myocardial infarction in myocardial-infraction animal model.
FIG. 5c represents the inhibitory effect of the orally administered beta-glucan, arabinoxylan, arabinose and xylose on the myocardial infarction in myocardial-infraction animal model.

As results of the above experiments, the IA (% AAR) of HY6228-treated group (n=9) and starch-treated group (n=8, SW) were 42.3 and 40.6%, respectively, whereas that of control group (n=57) was 51.8%. The results indicate that the size of infarcted area had been reduced by 18.3 and 21.6% ($p<0.05$) for HY6228-treated group and starch-treated group, respectively, confirming that starch has as much efficacy as crude extract in preventing myocardial infarction (See FIG. 5a). In addition, the IA (% AAR) of inventive dietary fiber-treated group (n=9; TDF) was 40.2%, meaning that the size of infarcted area had been reduced by 22.4% ($p<0.05$), compared with that of control group. Therefore, it was confirmed that dietary fiber also has as much efficacy as the crude extract in preventing myocardial infarction (See FIG. 5b).

Also, the IA (% AAR) of beta-glucan-treated group (n=12, b-glu 10), arabinoxylan-treated group (n=6, AX 10), arabinose-treated group (n=11, ara 10) and xylose-treated group (n=6, xyl 10), respectively, were 43.8, 42.3, 43.4 and 42.1%, respectively, whereas that of control group (n=29, control) was 50.6%. The results indicate that the size of infarcted area had been reduced by 13.4, 16.4, 14.2 and 16.8% for beta-glucan-, arabinoxylan-, arabinose-, and xylose-treated group, respectively ($p<0.05$), confirming that the representative components of total dietary fiber has as much efficacy as the crude extract in preventing myocardial infarction (See, FIG. 5c).

Experimental Example 5

Effect of Starch and Total Dietary Fiber Administered Orally on Cerebral Infarction (In Vivo)

The therapeutic efficacy of inventive starch and total dietary fiber on cerebral infarction was measured in cerebral infarction-induced rat model, using experiment rats prepared in Reference Example 1, in accordance with the procedure disclosed in the literature (Han H S et al., *J. Neurosci.*, 22, pp 3921-3928, 2002), with minor modification.

The SD rats prepared in Reference Example 1 were anesthetized by inhalation using enflurane (Choongwae Pharm. Corp., KOREA). The neck of rats was incised, carotid artery was exposed, and carotid artery and the external carotid artery were ligated. And then 3-0 nylon thread was inserted into the internal carotid artery to occlude the middle cerebral artery (MCA), resulting in ischemia. 400 mg/kg/day (0.5 ml) of HY6228 prepared in Example 1 and the inventive starch prepared in Example 2, and 50 mg/kg/day (0.5 ml) of the inventive total dietary fiber prepared in Example 2 had been administered orally thereto from 7 days to 1 day before ischemia was induced by surgery. Two hours after ischemia, the MCA blood flow was recovered by removing the thread. 22 hours after reperfusion, the cerebral-infarcted rats were induced to euthanasia and the brain was delivered to stain with the TTC solution. The infarct volume of cerebral hemisphere was measured with image analysis system (Quantity One 4.2, Bio-rad, USA).

Efficacy was compared with ischemic index (%), calculated as shown in Math Formula 1.

$$\text{Ischemic index}(\%) = A/B \times 100 \qquad \text{Math Figure 1}$$

A: infarcted volume of the cerebral hemisphere ($mm^3$)
B: total volume of cerebral hemisphere ($mm^3$)

As the result, the ischemic index of inventive starch-treated group (n=6, SW) was 74.5%, while that of the control group (n=12, control) was 93%.

Figure 6:
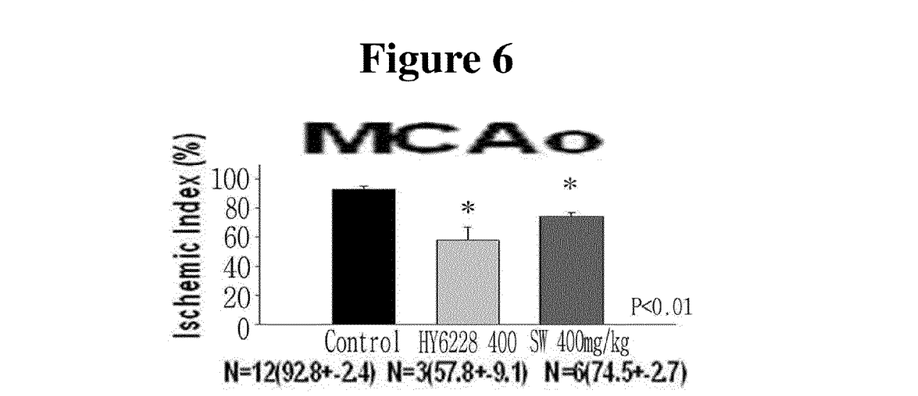
FIG. 6 presents the inhibitory effect of the orally administered inventive starch purified from *Triticum aestivum* L. on the cerebral infarction in cerebral-infraction animal model.

The results indicate that the size of infarcted area had been reduced by 19.7% ($p<0.05$), confirming that the inventive starch of the present invention has efficacy in preventing cerebral infarction (See, FIG. 6).

Experimental Example 6

Effect of Starch and Total Dietary Fiber Administered Orally on Dementia Induced by Scopolamine by Oral Administration (In Vivo)

The therapeutic efficacy of inventive crude extract, starch and total dietary fiber of the present invention on the memory impairment was determined by using scopolamine-induced dementia animal model, in which scopolamine acts as an antagonist to acetylcholine receptor, in accordance with the procedure cited in the literature (Fan et al., *Neurosci. Lett.* 374 pp 222-226, 2005) with minor modification.

The inventive starch and total dietary fiber prepared in Examples were orally administered to the rats prepared in Reference Example 1 for 12 consecutive days as test groups. Physiological saline was treated as negative control group. From the $8^{th}$ day of administration of the inventive starch and the fiber, 0.5 mg/kg of scopolamine was started to be injected intraperitoneally into the rats for another 5 days. From the same $8^{th}$ day of administration of the inventive starch and the fiber, water-maze test was also performed everyday to measure degree of memory loss for another 5 days.

Water-maze test was performed in a water tank which consisted of circular tub (inner dimensions: diameter 180 cm, depth: 50 cm) filled with water at a temperature of approximately 22-23° C. and escape platform (diameter: 10 cm, height: 25 cm) submerged 2 cm below the surface of the water. The movements of rats were recorded automatically by a video-tracking system (EthoVision, Noldus Information Technology, Wageningen, The Netherlands).

At the test, "escape latency" is the time(s) taken for the rats to find and escape onto the submerged platform, and, out of escape latencies measured, those that the rats stayed on the platform over 30 sec were counted effective. "Mean escape latency" is the average time(s) of three trials per day per rat. Therefore, fifteen trials per rat was performed for the five day's period of water-maze test. The same cut-off time of 90 sec was set in a case that the mean escape latency exceeds over 90 sec.

Before induction of dementia, 200 mg/kg of the inventive HY6228 prepared in Example 1 and the inventive starch prepared in Example 4, and 50 mg/kg of the inventive total dietary fiber prepared in Example 2 (Test group) or saline (Sham group) were administered orally. From the $8^{th}$ day of administration of the inventive starch and the fiber, 0.5 mg/kg of scopolamine was started to be injected intraperitoneally into the rats and water-maze test was also performed everyday, both for another 5 days.

Figure 7:
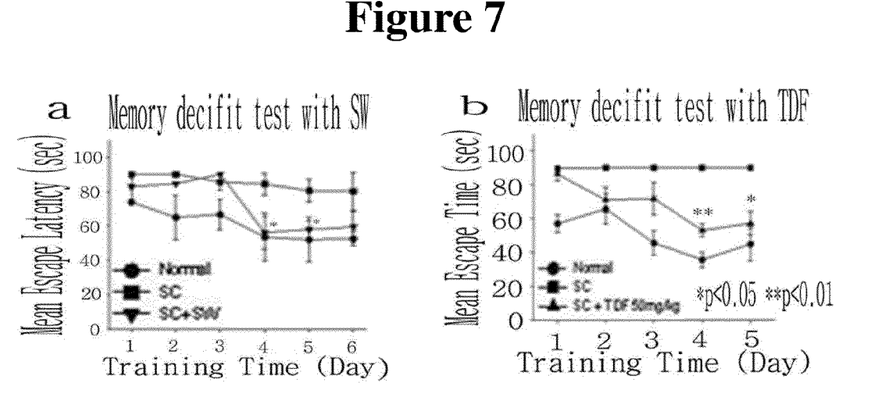
FIG. 7a presents the inhibitory effect of the orally administered inventive starch purified from *Triticum aestivum* L. on memory loss, measured by water-maze test in dementia-induced animal model.
FIG. 7b presents the inhibitory effect of the orally administered inventive TDF purified from *Triticum aestivum* L. on memory loss, measured by water-maze test in dementia-induced animal model.

As a result, there showed a significant decrease in the mean escape latency for test group treated with inventive starch and scopolamine (SC+SW, n=4) compared with scopolamine alone-treated group used as a negative control (SC, n=5) at the $4^{th}$ and $5^{th}$ day among the 6 days training period (p<0.05, FIG. 7a), although the mean escape latency for the test group was a little bit longer than that for the sham group (Normal, n=3). Additionally, there also showed a significant decrease in the mean escape latency for test group treated with TDF and scopolamine (SC+TDF, n=7) compared with scopolamine alone-treated group used as a negative control (SC, n=4) at the $4^{th}$ and $5^{th}$ day among the 5 day's test (p<0.05, FIG. 7b). Accordingly, it has been confirmed that the inventive starch and total dietary fiber of the present invention could improve dementia by inhibiting memory loss.

Experimental Example 7

Effect of Wheat-Derived Starch and Total Dietary Fiber Administered Orally on Vascular Dementia (In Vivo)

The therapeutic efficacy of inventive starch and total dietary fiber of the present invention on vascular dementia was measured in vascular dementia-induced rat model, using experiment rats prepared in Reference Example 1, in accordance with the procedure disclosed in the literature (Cho K O et al., *J. Neurosci. Res.*, 83, pp 285-291, 2006), with minor modification.

The SD rats prepared in Reference Example 1 were anesthetized by inhalation using enflurane (Choongwae Pharm. Corp., KOREA). Two common carotid arteries were exposed by surgery and tied with thread using BCCAO (bilateral common carotid artery occlusion) method to reduce the blood flow rate into brain for 4 weeks. And then water-maze test disclosed in Experimental Example 6 was performed for 5 days.

7 days after the two common carotid arteries were tied, the rats were started to be fed with HY6228 (200 mg/kg), inventive starch (SW; 200 mg/kg), TDF (50 mg/kg) and arabinoxlyan (50 mg/kg) therewith for 1 week, for which the mean escape latency was measured.

Figure 8:
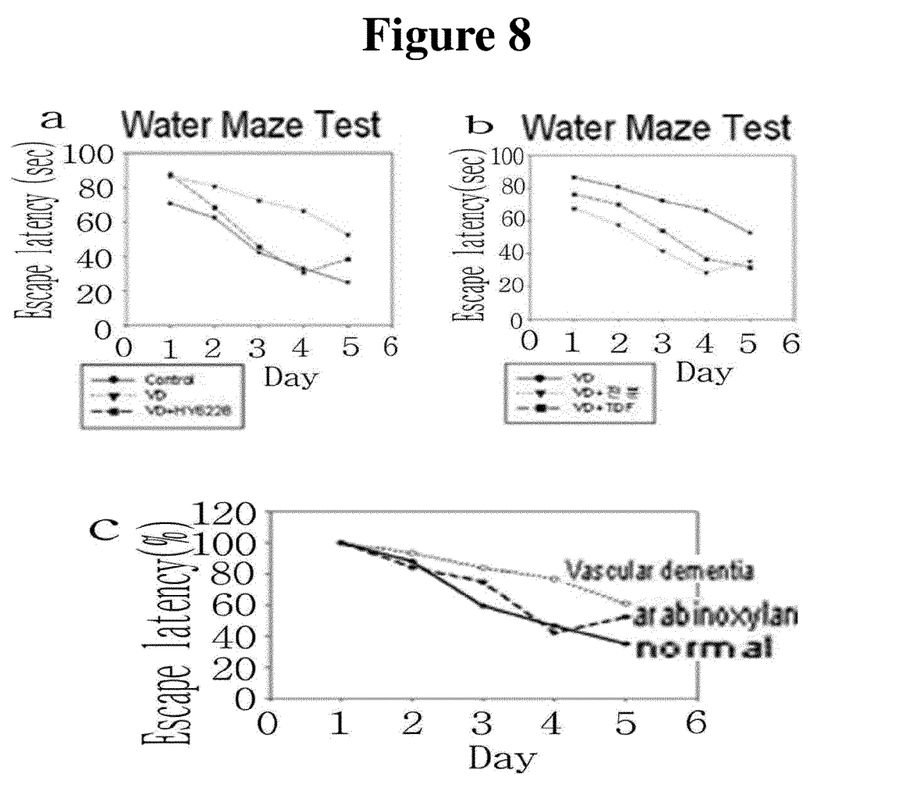
FIG. 8a presents the inhibitory effect of the orally administered inventive crude extract (HY6228) on dementia, measured by water-maze test in vascular-dementia animal model.
FIG. 8b presents the inhibitory effect of the orally administered inventive starch and TDF on dementia, measured by water-maze test in vascular-dementia animal model.
FIG. 8c presents the inhibitory effect of the orally administered arabinoxylan on dementia, measured by water-maze test in vascular-dementia animal model.

As the results, the mean escape latency of the group treated with HY6228 (VD+HY6228) on the $1^{st}$ day was similar to that of negative control (VD). However, it became similar to that of normal group (Control) on the $3^{rd}$ day, which shows that the group treated with HY6228 became accustomed to environmental circumstances more rapidly than that of negative control (VD) (See FIG. 8a).

Additionally, the groups treated with SW, TDF and arabinoxylan reduced the mean escape latency (See FIGS. 8b & 8c), which confirms that they are effective in treating vascular dementia.

Experimental Example 8

Toxicity Test

The acute toxicity tests on Sprague-Dawley rats (mean body weight 320±20 g) were performed using inventive starch (SW) prepared in Example 2. Two groups consisting of 5 rats were intraperitoneally and orally administered with 500 mg/kg and 5000 mg/kg of test sample, respectively.

When the rats were observed for 24 hours, there were no treatment-related effects on mortality, clinical signs, body weight changes and gross findings in any group. These results suggest that the inventive starch prepared in the present invention is safe.

Hereinafter, the formulating methods and kinds of excipient will be described, but the present invention is not limited to them. The representative preparation examples were described as follows.

Preparation of Powder
   TDF of Example 2300 mg
   Lactose 100 mg
   Talc 10 mg
   Powder preparation was prepared by mixing the above components and filling sealed package.

Preparation of Tablet
  SW of Example 3 50 mg
  Corn Starch 100 mg
  Lactose 100 mg
  Magnesium Stearate 2 mg
  Tablet preparation was prepared by mixing the above components and entabletting.
Preparation of Capsule
  SC of Example 3 50 mg
  Corn starch 100 mg
  Lactose 100 mg
  Magnesium Stearate 2 mg
  Capsule preparation was prepared by mixing the above components and filling gelatin capsule by conventional gelatin preparation method.
Preparation of Injection
  SR of Example 3 50 mg
  Distilled water for injection optimum amount
  pH controller optimum amount
  Injection preparation was prepared by dissolving active component, controlling pH to about 7.5 and then filling all the components in 2 ml ample and sterilizing by conventional injection preparation method.
Preparation of Liquid
  TDF of Example 2 100 mg
  Isomerized Sugar 10 g
  Mannitol 5 g
  Distilled water optimum amount
  Liquid preparation was prepared by dissolving active component, filling all the components and sterilizing by conventional liquid preparation method.
Preparation of Health Food
  SW of Example 3 1000 mg
  Vitamin mixture optimum amount
  Vitamin A acetate 70 microgram
  Vitamin E 1.0 mg
  Vitamin B1 0.13 mg
  Vitamin B2 0.15 mg
  Vitamin B6 0.5 mg
  Vitamin B12 0.2 microgram
  Vitamin C 10 mg
  Biotin 10 microgram
  Amide nicotinic acid 1.7 mg
  Folic acid 50 microgram
  Calcium pantothenic acid 0.5 mg
  Mineral mixture optimum amount
  Ferrous sulfate 1.75 mg
  Zinc oxide 0.82 mg
  Magnesium carbonate 25.3 mg
  Monopotassium phosphate 15 mg
  Dicalcium phosphate 55 mg
  Potassium citrate 90 mg
  Calcium carbonate 100 mg
  Magnesium chloride 24.8 mg
  The above-mentioned vitamin and mineral mixture may be varied in many ways. Such variations are not to be regarded as a departure from the spirit and scope of the present invention.
Preparation of Health Beverage
  TDF of Example 2 1000 mg
  Citric acid 1000 mg
  Oligosaccharide 100 g
  Apricot concentration 2 g
  Taurine 1 g
  Distilled water 900 ml
  Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method of treating a degenerative brain disease, comprising the steps of:
    administering to a human or mammal a component selected from the group consisting of isolated arabinoxylan, and a mixture of isolated arabinoxylan and isolated arabinose;
    together with a pharmaceutically acceptable carrier or adjuvant thereof, and
    wherein the degenerative brain disease is selected from the group consisting of Alzheimer's disease, vascular dementia, and Parkinson's disease.

2. The method according to claim 1, wherein the amount of the component administered is from 0.1 mg/kg/day to 1,000 mg/kg/day.

3. The method according to claim 1, wherein the component is the isolated arabinoxylan.

4. The method according to claim 3, wherein the degenerative brain disease is Alzheimer's disease.

5. The method according to claim 3, wherein the degenerative brain disease is vascular dementia.

6. The method according to claim 3, wherein the degenerative brain disease is Parkinson's disease.

7. The method according to claim 1, wherein the component is the mixture of isolated arabinoxylan and isolated arabinose.

8. The method according to claim 7, wherein the degenerative brain disease is Alzheimer's disease.

9. The method according to claim 7, wherein the degenerative brain disease is vascular dementia.

10. The method according to claim 7, wherein the degenerative brain disease is Parkinson's disease.

11. A method of treating a degenerative brain disease, comprising the steps of:
    administering to a human or mammal a component consisting of isolated arabinose;
    together with a pharmaceutically acceptable carrier or adjuvant thereof, and
    wherein the degenerative brain disease is selected from the group consisting of Alzheimer's disease, vascular dementia, and Parkinson's disease.

12. The method according to claim 11, wherein the degenerative brain disease is Alzheimer's disease.

13. The method according to claim 11, wherein the degenerative brain disease is vascular dementia.

14. The method according to claim 11, wherein the degenerative brain disease is Parkinson's disease.

15. A method of treating a degenerative brain disease, comprising the steps of:
    administering to a human or mammal a component consisting essentially of isolated arabinose;
    together with a pharmaceutically acceptable carrier or adjuvant thereof, and
    wherein the degenerative brain disease is selected from the group consisting of Alzheimer's disease, vascular dementia, and Parkinson's disease.

16. The method according to claim 15, wherein the degenerative brain disease is Alzheimer's disease.

17. The method according to claim 15, wherein the degenerative brain disease is vascular dementia.

18. The method according to claim 15, wherein the degenerative brain disease is Parkinson's disease.

* * * * *